(12) United States Patent
Shibasaki et al.

(10) Patent No.: US 6,615,670 B2
(45) Date of Patent: Sep. 9, 2003

(54) HIGH-SPEED ROTATION TESTING APPARATUS

(75) Inventors: Koji Shibasaki, Chiba (JP); Takeshi Watabe, Chiba (JP); Shiro Shibasaki, Chiba (JP)

(73) Assignee: Maruwa Electronic Inc., Chiba (JP)

( * ) Notice: Subject to any disclaimer, the term of this patent is extended or adjusted under 35 U.S.C. 154(b) by 0 days.

(21) Appl. No.: 10/067,396

(22) Filed: Feb. 7, 2002

(65) Prior Publication Data

US 2002/0112546 A1 Aug. 22, 2002

(30) Foreign Application Priority Data

Feb. 19, 2001 (JP) ........................................ 2001-041694

(51) Int. Cl.⁷ ............................................... G01B 7/16
(52) U.S. Cl. .......................................... 73/781; 73/761
(58) Field of Search ........................... 73/781, 760, 761

(56) References Cited

U.S. PATENT DOCUMENTS

| | | | | |
|---|---|---|---|---|
| 4,950,109 A | * | 8/1990 | Dettinger .................... | 408/82 |
| 5,804,737 A | * | 9/1998 | Johnson et al. .............. | 73/761 |
| 5,959,189 A | * | 9/1999 | Jeng et al. ................... | 73/10 |

FOREIGN PATENT DOCUMENTS

JP           7318456        12/1995

OTHER PUBLICATIONS

English Translation for JP 07–318456.*
English Language Abstract for JP Appln. No. 7–318456.

* cited by examiner

*Primary Examiner*—Max Noori
(74) *Attorney, Agent, or Firm*—Greenblum & Bernstein, P.L.C.

(57) ABSTRACT

A high-speed rotation testing apparatus includes a spindle 11 holding a test object S at its lower end, a driving motor 20 for applying torque to the spindle 11, and a frame 30 for supporting a rotor shaft 21 of the driving motor 20 so that the shaft is arranged toward the vertical direction of the apparatus, wherein the spindle 11 is driven directly by a driving motor 20 by inserting the spindle 11 into a through-hole 21a that penetrates the center of the rotor shaft 21 and coupling the upper ends of the rotor shaft 21 and the spindle 11 together, and the through-hole 21a has an inner diameter set so as to form a clearance in which the lower end of the spindle can swing, and further, a damping mechanism 40 that restrains swing is arranged in the vicinity of the lower end of the spindle 11, which projects from the lower end of the rotor shaft 21.

21 Claims, 6 Drawing Sheets

HIGH-SPEED ROTATION TESTING APPARATUS

BACKGROUND OF THE INVENTION

1. Field of the Invention

The present invention relates to a high-speed rotation testing apparatus, and in particular, to a high-speed rotation testing apparatus preferably used to check the performance and strength of a rotating member of a mechanical element of an apparatus for airplane engines, heavy electrical equipment, grinding stones, generators, ships, automobiles, etc.

2. Description of the Related Art

Conventional high-speed testing apparatuses will be described. The high-speed rotation testing apparatus generally tests industrial products (for example, fans and other rotating members) that are rotated during operation. The high-speed rotation testing apparatus rotates a test object at a rotation speed rated for the operation of the test object to test the reliability thereof under these conditions.

Further, in addition to the check on the rated rotation of the test object prior to incorporation into the actual machine described above (such as an airplane engine), the high-speed rotation testing apparatus is used for various other applications depending on its object, including checks on the safety during overspeed, checks on the rupture strength exhibited when centrifugal stress is forcibly applied, checks on the fatigue strength exhibited when the rotation speed is alternately increased and reduced for a long time (cycle test), tests in which the test object is permanently distorted, and tests in which a distortion gauge is stuck to the test object to measure the stress and distortion during rotation. Accordingly, this apparatus is essential in the industrial fields that use high-speed rotating parts. Recent high-speed rotation testing apparatuses mainly use two types of drive sources for rotation: one of these types uses an air turbine, and the other is based on a gear speed-increase motor driving method that uses a driving motor.

FIG. 5 shows a part of a high-speed rotation testing apparatus based on the air turbine method. The high-speed rotation testing apparatus 100 comprises an air turbine 102 that is rotated by receiving compressed air from a compressor 101, a support shaft 103 holding a test object S and is rotated by receiving torque applied by the air turbine 102, a storage section 105 that stores the test object S, supported by the support shaft 103, and a damper 107 for the support shaft 103. The test object S is an object shaped like a rotating member which has its durability under high-speed rotation tested as described previously.

The air turbine 102 comprises a casing 104 rotatably storing and supporting a rotor 106. Compressed air from the air compressor 101 blows against a bucket portion of the rotor 106 to apply a rotational force to the rotor 106. Thus, the rotor 106 outputs torque.

On the other hand, the casing 104 and the storage section 105 are integrated together. The casing 104 supports the rotor 106 so that when the casing 104 and the storage section 105, integrated together, are placed on a horizontal surface, the rotational center line of the rotor 106 is arranged toward the vertical direction of the apparatus. Further, the rotor 106 is concentrically fixed (connected) to the support shaft 103.

Furthermore, the test object S is held at the lower end of the support shaft 103. The support shaft 103 has a holding mechanism (not shown) provided at the lower end thereof. The holding mechanism fixes the rotating-member-shaped test object S concentrically to a rotating shaft at the rotational center of the test object S by, for example, bolting or screwing. Thus, the test object S rotates with the support shaft 103.

With this construction, when the compressor 101 is activated, the support shaft 103 and the test object S are rotated with the rotor 106. Then, the flow of compressed air from the compressor 101 is controlled so that the rotation speed of the test object S has the target value. Then, high-speed rotation tests are carried out for a predetermined time.

FIG. 6 shows a part of a high-speed rotation testing apparatus 200 using a driving motor as a drive source. The high-speed rotation testing apparatus 200 comprises a driving motor 201, a gear train 202 rotated by the driving motor 201, a support shaft 203 holding the test object S and is rotated by receiving torque from the gear train 202, a casing 204 for supporting the driving motor 201, the gear train 202, and the support shaft 203, a storage section 205 that stores the test object S supported by the support shaft 203, and a damper 210 for the support shaft 203.

The casing 204 and the storage section 205 are integrated together. The casing 204 supports the driving motor 201 so that when the casing 204 and the storage section 205, integrated together, are placed on a horizontal surface, a rotor shaft 201a of the driving motor 201 is arranged toward the vertical direction of the apparatus. The gear train 202 comprises a driving gear 206 and a driven gear 207 driven thereby. A support shaft 206a of the driving gear 206 is connected to the rotor shaft 201a, and a support shaft 207a of the driven gear 207 is fixedly and concentrically connected to the support shaft 203. The casing 204 supports the support shafts 206a, 207a, and 203 so that these shafts are arranged toward the vertical direction. The gear train 202 also serves to increase a rotation speed transmitted from the driving motor 201 to the support shaft 203. In the high-speed rotation testing apparatus 200 shown in FIG. 6, the gear train 202 is illustrated to be composed only of spur gears but may be composed of other various gears such as planetary, helical, and bevel gears. Alternatively, instead of the gear train, a belt may be used to transmit torque and increase the rotation speed.

Furthermore, the test object S is fixed at the lower end of the support shaft 203 via the above described support shaft 103 and a holding mechanism (not shown). Thus, the test object S rotates with the support shaft 203.

With this construction, when the driving motor 201 is rotated, the support shaft 203 and the test object S are rotated by the gear train 202. Then, the driving motor 201 is controlled so that the rotation speed of the test object S, achieved via the gear train 202, has the target value. In this manner, high-speed rotation tests are conducted as in the case with the high-speed rotation testing apparatus 100.

Long-time cyclic operation (the rotation speed of the rotating member is alternately set for an upper and a lower limit values) intended to check the fatigue strength of a rotating member represented by an airplane engine has recently frequently been performed in every field, for example, in the fields of research and trial production and product shipment. To such long-time tests, it is important to reduce tests costs and improve the maintainability of the testing apparatus.

The above described high-speed rotation testing apparatus 100 using the air turbine 102 allows easy maintenance owing to the simplified structure of the air turbine. Further, the high-speed rotation testing apparatus 100 must use the compressor 101 because compressed air is required to drive the air turbine. In this case, the rotor of the air turbine rotates using air as a medium, so that energy is prone to be lost when compressed air blows against the rotor to apply rotational force to the rotor. Accordingly, the air compressor 101 must provide about 37-kW power even for small-sized high-speed rotation testing apparatuses and 300-kW or more power for large-sized high-speed rotation testing apparatuses. Consequently, the high-speed rotation testing apparatus 100 disadvantageously consumes a huge amount of power for the above described tests requiring a long-time continuous operation. Further, since the compressor 101 generates heat, it is disadvantageously difficult to operate the high-speed rotation testing apparatus for a long time. Furthermore, although the high-speed rotation testing apparatus 100 controls the rotation speed of the test object S by controlling the flow of compressed air from the air compressor 101, it is difficult to precisely control the rotation speed of the test object S because air is used as a medium for applying torque to the rotor 106. Therefore, also owing to the difficulties with which the rotation speed of the test object S is controlled, the conventional high-speed rotation testing apparatus 100 is unsuitable for high-speed rotation tests that must be conducted for a long time.

On the other hand, the high-speed rotation testing apparatus 200 based on the gear speed-increase motor driving method and which uses the driving motor 201 as a drive source has the following disadvantages: The driving motor 201 comprises a rotor 208 and a stator 209, and the clearance between the rotor 208 and the stator 209 significantly affects output from the driving motor 201. That is, the rotor 208 vibrates in the direction of the rotational radius of the apparatus, and this vibration leads to an energy loss. Accordingly, it is necessary to reduce the vibration in the direction of the rotational radius, which occurs in the rotor 208. In the above described high-speed rotation tests in which the test object S is rotated at high speed or the rotation speed of the test object S is varied, the vibration in the direction of the rotational radius may occur notably in the support shaft 103. Therefore, the high-speed rotation testing apparatus 200 requires the gear train 202 to be interposed between the rotor shaft 201a and the support shaft 203.

However, when the gear train 202 is interposed between the driving motor 201 and the support shaft 203, the number of required parts such as gears, support shafts, and bearings therefor increases. Thus, disadvantageously, the structure of the high-speed rotation testing apparatus becomes complicated, and the maintenance of the apparatus thus becomes difficult. Further, in the high-speed rotation testing apparatus 200 with the gear train 202 interposed between the driving motor 201 and the support shaft 203, mechanical losses may result from the engagement between the gear 206 and 207 and from the friction between the support shafts 206a and 207a and the bearings therefor. This hinders output from the driving motor 201 from being efficiently transmitted to the test object, thereby preventing the full use of the output. Further, adjustment of the rotation speed of the test object S may result in a variation in this rotation speed. Furthermore, because of the use of the gear train 202, noise may occur from the gear 206 or 207, or the gear train 202 itself may vibrate to adversely affect the test object S.

The above described mechanical losses may amount to at least about 20 to 30% of the output from the driving motor 201 and even to about 50% thereof, depending on the structure of the apparatus. Consequently, the duration per cycle of the above-described cyclic tests or the like increases during which the rotation speed is increased and reduced by, for example, setting an upper and a lower limit value therefor. As a result, the tests disadvantageously require a very long time. Further, it should be appreciated that the mechanical losses increase the power consumption of the driving motor and that the power consumption further increases owing to the extended duration of the tests.

As described above, although the high-speed rotation tests are frequently used for research and development and for products, the conventional high-speed rotation testing apparatus has the above described disadvantages, which hinder progress in the development of products requiring high-speed rotation.

BRIEF SUMMARY OF THE INVENTION

Object of the Invention

It is an object of the present invention to provide a high-speed rotation testing apparatus that improves the disadvantages of the conventional examples and in particular improves maintainability, reduces tests costs, and has a simplified structure.

Summary of the Invention

The present invention provides a high-speed rotation testing apparatus for rotating a test object to check strength and durability thereof under the rotation, the apparatus comprising a spindle holding the test object at a lower end thereof, a driving motor for applying torque to the spindle, and a frame for supporting a rotor shaft of the driving motor so that the rotor shaft is arranged toward a vertical direction.

The spindle is inserted into a through-hole formed in a center of the rotor shaft, and an upper end of the rotor shaft and an upper end of the spindle are fixed together, thereby allowing the spindle to be driven directly by the driving motor. The through-hole having an inner diameter for allowing a clearance in which the lower end of the spindle can swing, and a damping mechanism for restricting the pivoting is arranged close to the lower end of the spindle projecting from the lower end of the rotor shaft.

In the present invention, the "frame for supporting the rotor shaft so that the rotor shaft is arranged toward a vertical direction" means that when the frame is ready for high-speed rotation tests (for example, it is installed on a horizontal surface), it supports the rotor shaft so that the shaft is arranged toward the vertical direction.

With the above configuration, the spindle holding the test object is installed in the through-hole formed in the rotor shaft of the driving motor. Thus, no gear train is interposed between the rotor shaft and the spindle as in the conventional high-speed rotation testing apparatus. This prevents the degradation of maintainability and mechanical losses which are caused by an increase in the number of parts associated with the provision of the gear train.

The rotor shaft and the spindle are connected together only at the upper ends thereof. Further, the damping mechanism is arranged in the vicinity of the lower end of the spindle to restrict it from vibrating. Furthermore, the clearance is formed between the spindle and the through-hole at the location corresponding to the middle of the spindle. Without any clearance between the spindle and the through-hole in the rotor shaft, if the center of gravity of the test object is offset from the center line of the spindle, that part of the spindle which projects from the lower end of the rotor shaft may be deflected in the direction of the rotational radius of the apparatus, causing the spindle to be broken down. Further, vibration caused by the deflection of the spindle is transmitted directly to the rotor of the driving motor, resulting in a failure or defect in the driving motor.

However, in the present invention, the clearance between the through-hole and the spindle allows the entire spindle to swing around the upper end thereof. This avoids concentrating stress on the part of the spindle which projects from the lower end of the rotor shaft.

Furthermore, the spindle is damped by the damping mechanism in the vicinity of the test object, which may cause vibration. Accordingly, even if that part of the spindle on which the test object is held, that is, the vicinity of the test object, is vibrated in the direction of the rotational radius occurs in, energy obtained by swing spindle is transmitted to the frame.

Further, the spindle is fixed to the rotor shaft at the upper end thereof which is located remote from the test object. Thus, even if that part of the spindle on which the test object is held is vibrated in the direction of the rotational radius, this vibration is converted into swing around the upper end of the spindle. Thus, the vibration occurring at the upper end of the spindle has only a small displacement and is thus sufficiently restrained from being transmitted from the upper end of the spindle to the upper end of the rotor shaft.

Therefore, according to the present invention, high-speed rotation tests can be carried out by efficiently transmitting the torque of the driving motor to the test object, while eliminating the defects of the gear train.

The construction of another high-speed rotation testing apparatus, which is different from the above, will be described below. This high-speed rotation testing apparatus comprises a spindle holding the test object at a lower end thereof, a driving motor for applying torque to the spindle, a weight supporting shaft having a through-hole in a center thereof, the through-hole being penetrated by the spindle, and a frame for supporting a rotor shaft of the driving motor and the weight supporting shaft so that these shafts are arranged toward a vertical direction.

The rotor shaft and the spindle are connected together so that center lines of the rotor shaft and the spindle are aligned with each other, and the spindle extends below a lower end of the rotor shaft. Further, the spindle is inserted into the through-hole in the weight supporting shaft, and an upper end of the weight supporting shaft is connected to the spindle. The frame rotatably supports the weight supporting shaft via a thrust bearing. The through-hole in the weight supporting shaft having an inner diameter for allowing a clearance to be formed in which the lower end of the spindle can swing, and a damping mechanism is arranged for restricting the swing of a vicinity of the lower end of the spindle projecting from the lower end of the weight supporting shaft.

In this high-speed rotation testing apparatus, which is different from the high-speed rotation testing apparatus described previously, the spindle is inserted into the weight supporting shaft below the rotor shaft, the weight supporting shaft comprising the through-hole providing the clearance. Then, the upper end of the weight supporting shaft is connected to the spindle, and the damping mechanism damps the spindle below the weight supporting shaft.

With this construction, the spindle may vibrate around the junction between the spindle and the upper end of the weight supporting shaft, but this vibration is restrained by the damping mechanism. Accordingly, during swing, the spindle may be bent between the junction between the spindle and the weight supporting shaft and the lower end of the spindle.

Furthermore, the swing of the spindle is restricted by the damping mechanism, thereby avoiding the breakdown of the spindle resulting from stress concentration as in the case with the previously shown high-speed rotation testing apparatus. Since the upper end of the weight supporting shaft supported by the thrust bearing and the spindle are connected to each other, the swing of the spindle is not transmitted above the junction, thereby influence of the swing of the spindle on the rotor shaft being avoided. Thus, this high-speed rotation testing apparatus have the same advantages as the high-speed rotation testing apparatus initially described.

Furthermore, since the weight supporting shaft supported by the frame and the spindle is connected to each other via a thrust bearing, even if a test subject with large weight is attached to the spindle, the weight load of the subject is applied to the frame through the weight supporting shaft. Accordingly, this high-speed rotation testing apparatus allows a high-speed rotation testing for a test subject with a larger weight than the case of the high-speed rotation testing apparatus initially described.

Further, the above described damping mechanism may have a journal bearing corresponding to the spindle, a housing for supporting the journal bearing, and a storage chamber formed in the frame and which holds the housing so that it can swing with the spindle, the storage chamber being filled with a lubricant.

In this case, the spindle is inserted into the journal bearing with a clearance formed therebetween, and the lubricant flows into the clearance. When the spindle rotates at high speed, the lubricant serves to exert film pressure against the spindle to guide the journal bearing so that the spindle is located at the center of the journal bearing. At this time, the spindle is subjected to resistance from the lubricant flowing through the clearance in the journal bearing. Furthermore, as the spindle swings, the journal bearing swings responsively. However, the lubricant is already present between the journal bearing and the housing, so that when the journal bearing swings relative to the housing, it undergoes flow resistance from the lubricant.

On the other hand, the housing, supporting the journal bearing, is subjected to reaction from the journal bearing via the lubricant and guided in the same direction as that in which the spindle is guided. Accordingly, when the spindle is vibrated in the direction of the rotational radius (swing around the upper end of the spindle), the housing swings similarly to the spindle, but undergoes flow resistance from the lubricant again because it is inside the storage chamber, filled with the lubricant.

That is, during swing, the spindle undergoes all the flow resistance from the lubricant between the spindle and journal bearing, between the journal bearing and the housing, and between the housing and the storage chamber. Consequently, these viscous resistances serve to damp the spindle to restrain it from swing.

Alternatively, the spindle may be extended downward so that a sufficiently long part of the spindle projects from the lower end of the rotor shaft, and the projecting part may be supported by the frame via the thrust bearing. In this case, since the load of the test object is supported by the frame via the thrust bearing, heavier test objects can be subjected to high-speed rotation tests.

Further, the above described construction of the present invention may include a storage container in which the test object held by the spindle is stored to prevent crushed pieces of the test object from scattering. Furthermore, the storage container is desirably a vacuum vessel from which an internal gas can be discharged. The storage container enables high-speed rotation tests to be carried out up to the limits beyond which the test object is broken down. Further, if the storage container is a vacuum vessel, the periphery of the test object can be formed into a vacuum before the tests. Consequently, windage losses are eliminated to enable the rotation speed to be promptly increased up to a target value.

The present invention attains the object described previously, using the above described constructions.

DETAILED DESCRIPTION OF THE PREFERRED EMBODIMENTS (First Embodiment)
(Outline)

Figure 1:
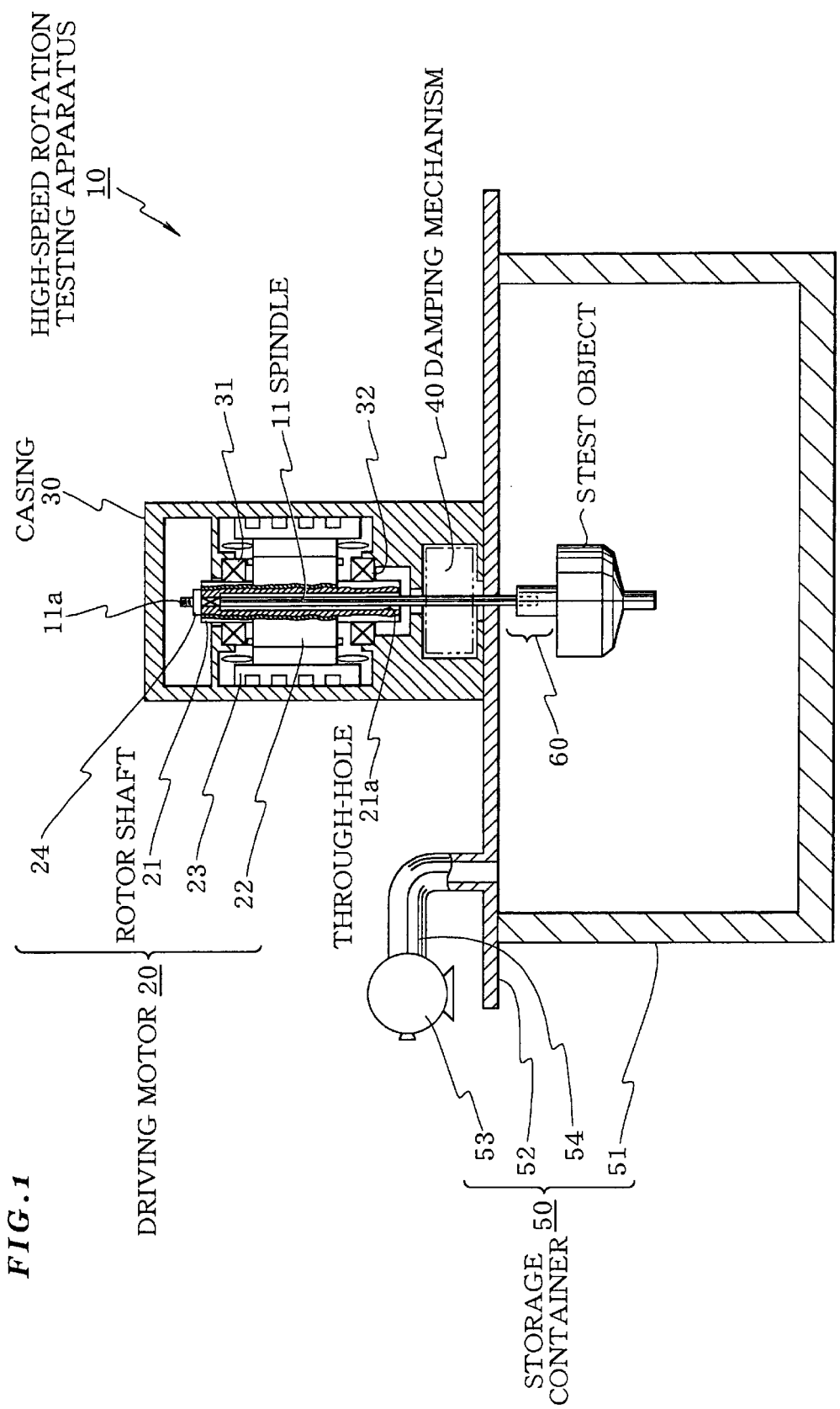
FIG. 1 is a schematic vertical sectional view of a high-speed rotation testing apparatus as a first embodiment of the present invention as viewed from the front thereof.
Figure 2:
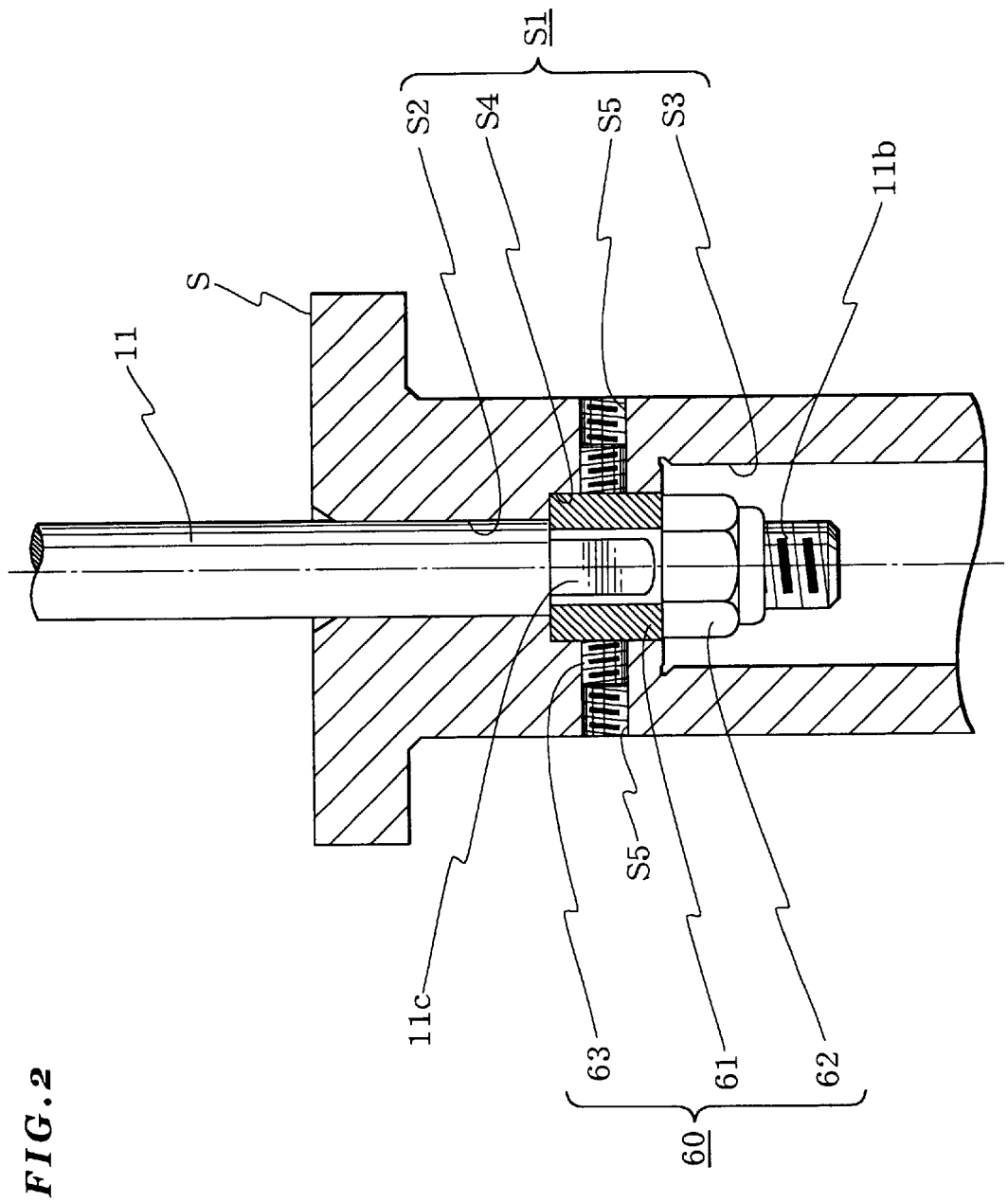
FIG. 2 is a view illustrating a holding state, showing an example of a holding means provided in the high-speed rotation testing apparatus.

A first embodiment of the present invention will be described with reference to FIGS. 1 to 3. FIG. 1 is a schematic vertical sectional view of a high-speed rotation testing apparatus 10 according to this embodiment as viewed from the front thereof. The high-speed rotation testing apparatus 10 rotates a test object S as a rotating member at high speed to check its strength, durability, or the like under the rotation.

The high-speed rotation testing apparatus 10 comprises a spindle 11 holding the test object S at the lower end thereof, a driving motor 20 for applying torque to the spindle 11, a casing 30 as a frame which supports a rotor shaft 21 of the driving motor 20 so that the shaft is arranged toward the vertical direction of the apparatus, a damping mechanism 40 arranged in the vicinity of the lower end of the spindle 11 to restrain the lower end from vibrating in the direction of the rotational radius of the apparatus, and a storage container 50 that stores the test object S held by the spindle 11 so as to prevent crushed pieces of the test object S from scattering. Each of these components will be described below.

[Casing]

The casing 30 is integrally formed on the storage container 50. The casing 30 is hollow and has the driving motor 20 and the damping mechanism 40 stored therein. With the storage container 50 horizontally installed, the casing 30 supports the rotor shaft 21 so that the shaft is arranged toward the vertical direction of the apparatus. Furthermore, the casing 30 rotatably supports the rotor shaft 21 via bearings 31 and 32 installed in the vicinity of the upper and lower ends of the rotor shaft 21.

[Driving Motor and Spindle]

The driving motor 20 comprises the rotor shaft 21 described previously, a rotor 22 that rotates inside the casing 30 together with the rotor shaft 21, and a stator 23 fixedly installed inside the casing 30 so as to surround the rotor 22.

The rotor shaft 21 has a through-hole 21a formed along the center line thereof and into which the spindle 11 is inserted. The through-hole 21a is formed to have a square cross section in the vicinity of the upper end thereof and a circular cross section in the other portions thereof. Further, each side of the square cross section of the through-hole is set smaller than the diameter of the circular cross section. On the other hand, like the through-hole 21a, the spindle 11 is formed to have a square cross section in the vicinity of the upper end thereof and a circular cross section in the other portions thereof. Each side of the square cross section of the spindle 11 is substantially as large as each side of the square cross section of the through-hole 21a so that the square cross section portion of the spindle 11 can be inserted into the square cross section portion of the through-hole 21a. Further, the diameter of the circular cross section of the spindle 11 is set slightly smaller than that of the circular cross section of the through-hole 21a. Furthermore, an external thread portion 11a is formed at the top of the square cross section portion of the spindle 11. When the spindle 11 is inserted into the rotor shaft 21 from below and the square cross section portion of the spindle 11 is fitted in the square cross section portion of the trough-hole 21a formed in the rotor shaft 21, the external thread portion 11a of the spindle 11 projects from the upper end surface of the rotor shaft 21. The spindle 11 is fixed to the rotor shaft 21 by tightening the external thread portion 11a with a locknut 24. Since the rotor shaft 21 and the spindle 11 are fitted together at their square cross section portions, the spindle 11 is rotationally driven with the rotor shaft 21 by the driving motor 20.

Further, as described previously, a clearance is formed between the circular cross section portion of the through-hole 21a and the circular cross section portion of the spindle 11. In general, the circular cross section of the spindle 11 has an outer diameter of 4 to 80 mm depending on the weight of the test object. On the other hand, the clearance having a width of about 10 to 100 $\mu$m depending on the diameter of the spindle 11. That is, this width is generally set equal to about one-eight-hundred-th to one-four-hundred-th of the outer diameter of the spindle 11 but may be set to have a larger value. The outer diameter of the spindle 11 is not limited to the above-described range and may be set to have a smaller or larger value. Further, the ratio of the clearance to the outer diameter of the spindle is not limited to the above-described range. Within the clearance of the through-hole 21a in the rotor shaft 21, the lower end of the spindle 11, on which the test object S is held, can be swung using the upper end as a support point.

Furthermore, the spindle 11 has a length set larger than that of the rotor shaft 21, and its lower end projects from the lower end of the casing 30 and leads to the interior of the storage container 50.

[Holding Means]

The spindle 11 has a holding means 60 provided at its lower end to fixedly hold the test object S. The holding means 60 is constructed differently depending on the shape or structure of the test object S. Accordingly, the holding means 60 is not limited to the one described below, but an example is shown in FIG. 2.

First, it is prerequisite that the spindle 11 has an external thread portion 11b formed at the lower end thereof and having a smaller diameter than the circular cross section of the spindle 11. Further, a second square cross section portion 11c is formed upwardly adjacent to the external thread portion 11b, the square cross section portion having substantially the same size as the square cross section portion of the spindle 11 described previously. On the other hand, the test object S has a center hole S1 formed along its center line passing through the center of gravity. The center hole S1 is structured to include two stages, and comprises a small diameter portion S2 arranged at its upper end, a large diameter portion S3 arranged below the small diameter portion S2, and an intermediate diameter portion S4 arranged between the small and large diameter portions. The small diameter portion S2 has a circular cross section into which the spindle 11 is inserted without any clearance, and the large diameter portion S3 has a larger circular cross section. Further, the intermediate diameter portion S4 has a polygonal cross section larger than the small diameter portion and smaller than the large diameter portion S3. Furthermore, the test object S has a plurality of tapped holes S5 radially formed around the center line of the center hole S1 and penetrating the test object from the exterior to the intermediate diameter portion S4. The tapped holes S5 are each formed so as to correspond to one of the sides of the polygon constituting the cross section of the intermediate diameter portion S4.

On the other hand, the holding means 60 comprises a sleeve 61 fitted in the intermediate diameter portion S4, a clamping bolt 62 screwed on the external thread portion 11b of the spindle 11, and a plurality of set screws 63 with hexagonal hole which are screwed into the tapped holes S5. The sleeve 61 is a polygonal column having an external cross section equal to that of the intermediate diameter portion S4. Further, the sleeve 61 has a through-hole formed in the center thereof and having a cross section equal to that of the second square cross section portion 11c. Accordingly, the sleeve 61 engages with both the spindle 11 and the test object S so as to transmit torque from the spindle 11 to the test object S. The clamping bolt 62 clamps the sleeve 61 from below to fix the sleeve 61 and the test object S to the spindle 11. Furthermore, the set screws 63 with hexagonal hole are abutted against the respective sides of the sleeve 61 and tightened so that the center of gravity of the test object S is on the center line of the spindle 11.

The cross sections of the intermediate diameter portion S4 and the sleeve 61 may be polygons having at least three angles. Further, the number of the tapped holes S5 and the set screws 63 with hexagonal hole may correspondingly be three or more. Furthermore, the previously described construction of the holding means 60 is varied so as to correspond to the shape or the like of the test object S. For example, if the test object S does not have the center hole S1 in which the spindle 11 can be directly installed, a jig having a similar center hole S1 may be used.

Further, the sleeve 61 and the intermediate diameter portion S4 may have circular cross sections, and holes in which the set screws 63 with hexagonal hole are received may be formed in the outer periphery of the circular cross section. Furthermore, in addition to the above-described holding means, a second holding means may be provided which is arranged in the storage container 50 and which rotatably holds the lower end of the test object S.

[Damping Mechanism]

Now, the damping mechanism 40 will be described. FIG. 3 is a sectional view taken along the center line of the spindle 11 and showing the damping mechanism 40 in detail. The damping mechanism 40 is arranged under the casing 30 and engaging with the vicinity of the lower end of the spindle 11 (above the holding means 60).

The damping mechanism 40 has journal bearings 41 and 42 that are bushing metals engaging with the spindle 11, a housing 44 holding the journal bearings 41 and 42, and a storage chamber 45 formed in the casing 30 and which holds the housing 44 so that it can swing with the spindle 11, the storage chamber being filled with a lubricant.

Figure 3:
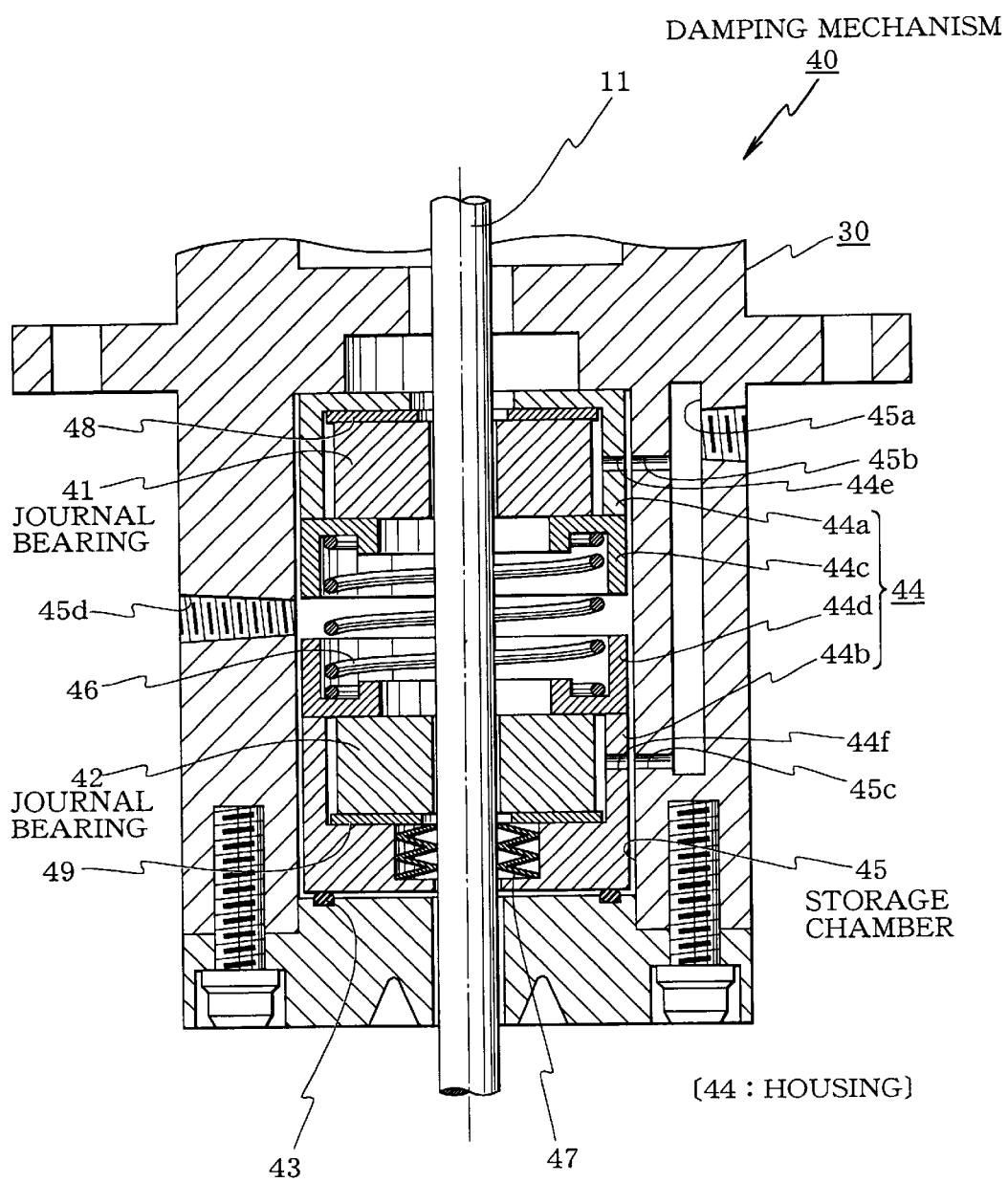
FIG. 3 is a detailed sectional view of a damping mechanism, taken along the center line of a spindle.

As shown in FIG. 3, the housing 44 is generally shaped like a cylinder the center of which is penetrated by the spindle 11. The storage chamber 45 is a space shaped correspondingly to the housing 44 so that the housing 44 can be stored therein with a small clearance. The casing 30 has a lubricant chamber 45a formed inside the casing 30 and to which a lubricant can be externally supplied through it is located adjacent to the storage chamber 45. The casing 30 has two supply ports 45b and 45c formed therein to supply a lubricant from the lubricant chamber 45a to the storage chamber 45. Further, the casing 30 has a discharge port 45d formed therein and through which a lubricant can be discharged from the storage chamber 45. Consequently, while the high-speed rotation testing apparatus 10 is operating, a lubricant can circulate through the storage chamber 45 so as to always fill it.

The housing 44 is composed of an upper cylinder 44a located at the top thereof, a lower cylinder 44b located at the bottom thereof, and two pressure sleeves 44c and 44d that press the cylinders 44a and 44b along the vertical direction so that the cylinders move away from each other.

The upper cylinder 44a has a cylindrical shape including a roof plate at the top thereof. A through-hole is formed in the center of the roof plate so that the spindle 11 can be loosely inserted into the through-hole. The upper cylinder 44a is arranged in the storage chamber 45 in such a way that the roof plate abuts against the inner wall surface of the top of the storage chamber 45. Further, the upper cylinder 44a has one 41 of the journal bearings stored therein.

The lower cylinder 44b has a cylindrical shape including a bottom plate at the bottom thereof. A through-hole is formed in the center of the bottom plate so that the spindle 11 can be loosely inserted into the through-hole. The lower cylinder 44b is arranged in the storage chamber 45 in such a way that the bottom plate abuts against the inner wall surface of the bottom of the storage chamber 45. Further, the lower cylinder 44b has the other journal bearing 42 stored therein.

Further, the cylinders 44a and 44b have through-holes 44e and 44f, respectively, formed in peripheral walls thereof to supply a lubricant to the interior thereof. The through-holes 44e and 44f are located so as to correspond to the two supply ports 45b and 45c, respectively, through which a lubricant is supplied to the interior of the storage chamber 45.

The pressure sleeves 44c and 44d each have a substantially annular bottom plate having the spindle 11 loosely inserted into the center thereof. A cylindrical side wall is provided at the outer edge of the bottom plate so as to stand up therefrom. The pressure sleeves 44c and 44d are arranged in the storage chamber 45 so that their bottom plates abut against the upper and lower cylinders 44a and 44b, respectively. A pressure spring 46 is interposed between the pressure sleeves 44c and 44d to press them away from each other.

Accordingly, the upper cylinder 44a has its roof plate pressed against the inner wall surface of the top of the storage chamber 45 via the pressure sleeve 44c. On the other hand, the lower cylinder 44b has its bottom plate pressed against the inner wall surface of the bottom of the storage chamber 45 via the pressure sleeve 44d. In this case, an O ring 43 is interposed between the bottom plate of the lower cylinder 44b and the inner wall surface of the bottom of the storage chamber 45 to prevent the lubricant present between the periphery of the housing 44 and the inner wall surface of the storage chamber 45 from leaking downward. Further, the lower cylinder 44b has an oil seal 47 stored in the bottom thereof and provided so as to surround the periphery of the spindle 11. The oil seal 47 prevents a lubricant in the housing 44 from leaking downward along the spindle 11.

Furthermore, the cylinders 44a and 44b and the pressure sleeve 44c and 44d, which constitute the housing 44, have substantially the same outer diameter, which is set so that a small clearance is formed between this outer diameter and the inner diameter of the storage chamber 45. This clearance is set at, for example, 0.2 mm. However, the clearance is not limited to this value because it is varied depending on the outer diameter of the housing 44.

The journal bearings 41 and 42 each have a central hole penetrated by the spindle 11 and having an inner diameter set slightly larger than the outer diameter of the spindle 11. Consequently, when the spindle 11 is inserted into the central holes in the journal bearings 41 and 42, a clearance is formed between both the inner walls of the journal bearings 41 and 42 and the peripheral surface of the spindle 11. As described previously, a lubricant is supplied to the journal bearings 41 and 42 and thus flows into the clearance between both the journal bearings 41 and 42 and the spindle 11. In this state, when the spindle 11 rotates at high speed in the journal bearings 41 and 42, film pressure is exerted against the spindle 11. The film pressure acts in such a direction that the spindle 11 is guided to the centers of the central holes of the journal bearings 41 and 42.

Further, the journal bearings 41 and 42 each have an outer diameter set so that a larger clearance is formed between each of the outer diameters of the journal bearings 41 and 42 and the corresponding one of the inner peripheral walls of the cylinders 44a and 44b (the size of the clearance is, for example, 0.5 mm, but is not limited to this value because it depends on the size of the housing) The clearance between each of the outer peripheral surface of the journal bearings 41 and 42 and the corresponding one of the inner peripheral walls of the cylinders 44a and 44b is set larger than the clearance between the both the central holes of the journal bearings 41 and 42 and the spindle 11. Washers 48 and 49 are interposed between the journal bearings 41 and 42 and the cylinders 44a and 44b, respectively, to allow the journal bearings 41 and 42 to function as bearings for the cylinders 44a and 44b.

Accordingly, when the spindle 11 swings while the spindle 11 is rotating at high speed, the journal bearings 41 and 42 also swings owing to the film pressure associated with the lubricant between the spindle 11 and both the journal bearings 41 and 42. Further, at this time, the spindle 11 undergoes flow resistance from the lubricant in the clearance between the spindle 11 and both the journal bearings 41 and 42. Furthermore, when the journal bearings 41 and 42 swing, they undergo flow resistance from the lubricant in the clearance between both the journal bearings 41 and 42 and the housing 44. Then, the housing 44 also swings because of reaction force resulting from the swing of the journal bearings 41 and 42, but undergoes flow resistance from the lubricant in the clearance between the housing 44 and the storage chamber 45. Consequently, during swing, the spindle 11 is subjected to flow resistance from the lubricant between the spindle 11 and both the journal bearings 41 and 42, between both the journal bearings 41 and 42 and the housing 44, and between the housing 44 and the storage chamber 45. Therefore, the spindle 11 is restrained from swing.

In this embodiment, the damping mechanism 40 is illustrated to comprise the journal bearings 41 and 42, the housing 44, the storage chamber 45, and others. However, the present invention is not limited to this construction, but the damping mechanism may have another construction based on the oil film or viscosity of the lubricant. Alternatively, the damping mechanism is not limited to the utilization of oil film or viscosity, but may be based on air, magnetic force, an elastic member, or the like.

[Storage Container]

Now, the storage container 50 will be described with reference to FIG. 1. The storage container 50 is composed of a bottomed cylindrical main body 51, a roof plate 52 that closes the top of the main body, a suction pump 53 that sucks air from the main body 51, and a line 54 that connects the suction pump 53 to the roof plate 52.

The top of the main body 51 is open, and a closed space is formed inside the main body 51 by fitting the roof plate 52 on the main body so as to cover this opening. A seal (not shown) is applied between the main body 51 and the roof plate 52. Further, the casing 30 is placed on the roof plate 52, and the lower end of the spindle 11 is loosely inserted into a through-hole formed in the center of the roof plate 52 and protrudes into the storage container 50. Since the test object S is attached to the lower end of the spindle as described previously, the test object S is stored in the storage container 50 after installation. The storage container 50 has the function of collecting broken pieces of the test object S scattered when the test object S is broken down during high-speed rotation tests. Accordingly, the main body 51 and the roof plate 52 are designed to have a strength sufficient to endure the collision of broken pieces. Further, for reinforcement, a plurality of stacked protective walls or a protective wall made of lead may be provided in the area composed of the main body 51 and the roof plate 52.

Further, before high-speed rotation tests, the air in the closed space formed of the main body 51 and roof plate 52 of the storage container 50 is discharged by the suction pump 53 until a vacuum is created in the closed space. The storage container 50 also functions as a vacuum vessel. This function is provided in order to prevent the test object S from suffering a windage loss and to enable the effects of centrifugal force on the test object S to be examined during high-speed rotation tests. Further, since the test object S suffers no windage loss, the rotation speed can be increased easily and promptly until it reaches the target speed.

[operation of the First Embodiment]

The general operation of the high-speed rotation testing apparatus 10 constructed as described above will be described with reference to FIG. 1. First, the holding means 60 is used to install the test object S on the lower end of the spindle 11. That is, the test object S is fixed to the lower end of the spindle 11 with the clamping bolt 62, and the center of gravity of the test object S is adjusted with the set screws 63 with hexagonal hole (see FIG. 2).

Subsequently, the storage container 50 is closed, and the suction pump 53 is used to create a vacuum in the storage container 50. Then, the driving motor 20 is driven to rotate the test object S at the target rotation speed via the spindle 11. Further, with a plurality of target rotation speeds, the rotation speed of the test object S is subsequently varied to each of the target values.

Before the tests, if the center of gravity of the test object S is located exactly on the center line of the rotor shaft 21 of the driving motor 20, the spindle 11 extends downward in the vertical direction and rotates stably. In this case, if the center of gravity is offset even slightly from the center line of the rotor shaft 21, the spindle 11 may be bent. However, the spindle 11 is fixed to the rotor shaft 21 at it supper end, which is remote from the test object S, and there is a clearance between the through-hole 21a and the spindle 11, so that the spindle 11 is gently bent around its upper end. This effectively avoids the concentration of stress at one location of the spindle 11, which may cause the spindle 11 to be broken down.

Furthermore, the spindle 11 engages with the damping mechanism 40, located in the vicinity of its lower end, so that the damping effect of the damping mechanism 40 restrains the spindle 11 from swing. Consequently, the test object S can be stably rotated at high speed even if its center of gravity is slightly offset from the center line of the rotor shaft 21.

[Effects of the First Embodiment]

As described above, in the high-speed rotation testing apparatus 10, the upper end of the spindle 11 is fixed to the upper end of the rotor shaft 21, so that the spindle 11 can swing around its upper end even if its center of gravity is slightly offset from the center line of the rotor shaft 21. Further, such swing is restrained by the damping mechanism 40, thereby minimizing the effects of vibration transmitted from the support point during swing to the rotor shaft 21. Consequently, in the high-speed rotation testing apparatus 10, by including no gear train in the construction of the apparatus 10, the driving motor 20 and the spindle 11 can be directly coupled together without damaging the driving motor 20. Therefore, the inconveniences associated with the presence of the gear train are eliminated.

(Second Embodiment)

Figure 4:
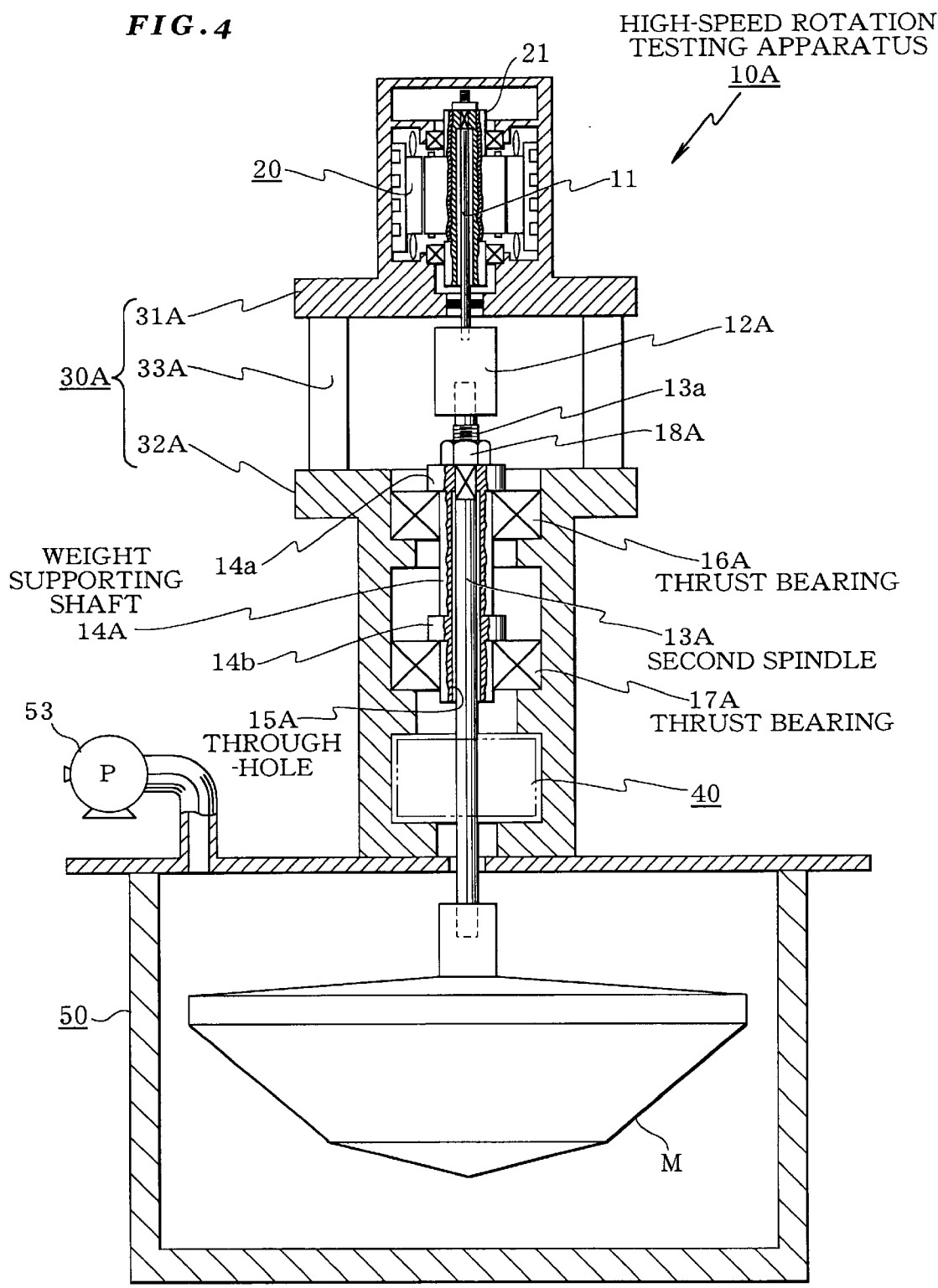
FIG. 4 is a schematic vertical sectional view of a high-speed rotation testing apparatus as a second embodiment of the present invention as viewed from the front thereof.
Figure 5:
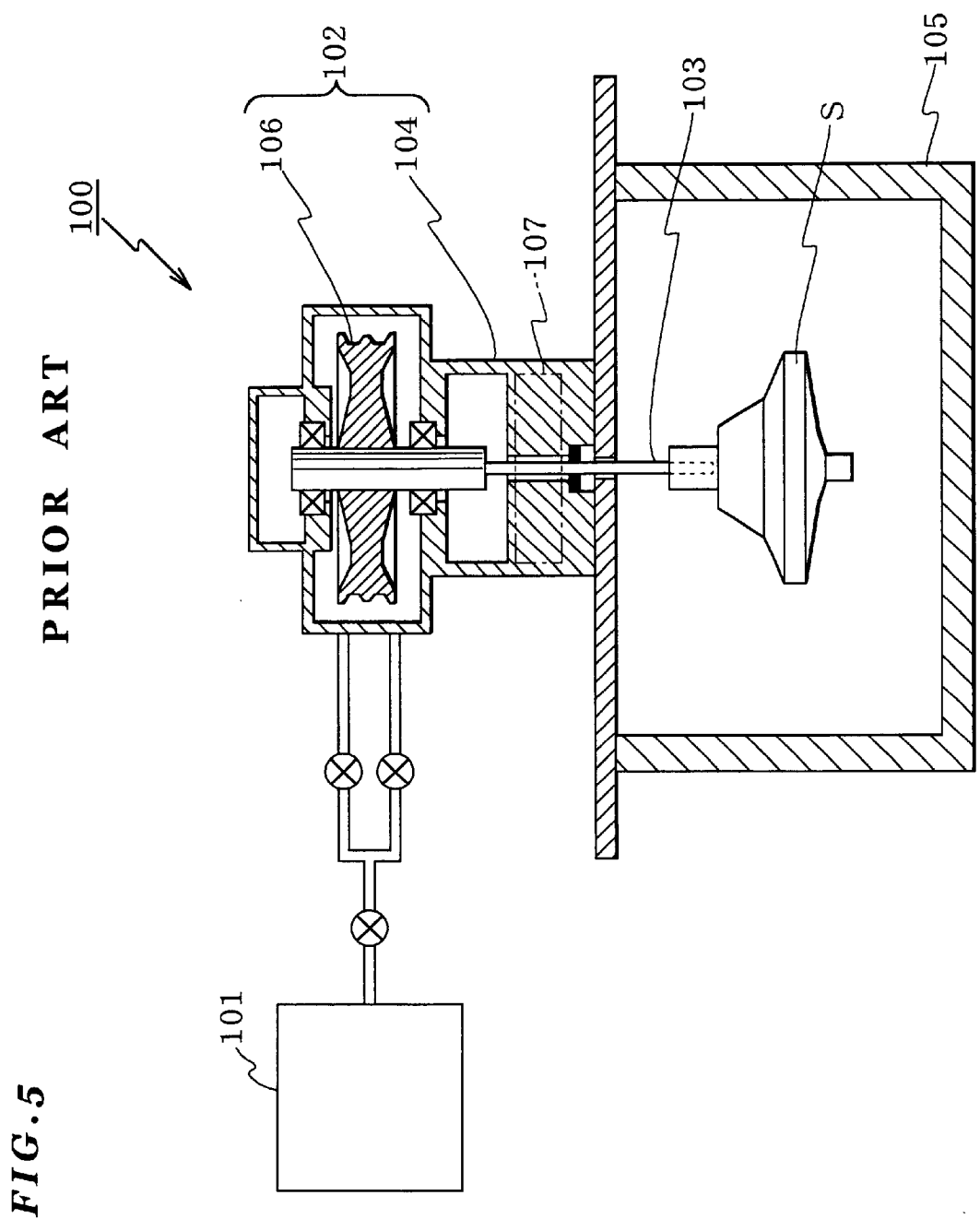
FIG. 5 is a schematic vertical sectional view of a conventional example as viewed from the front thereof.
Figure 6:
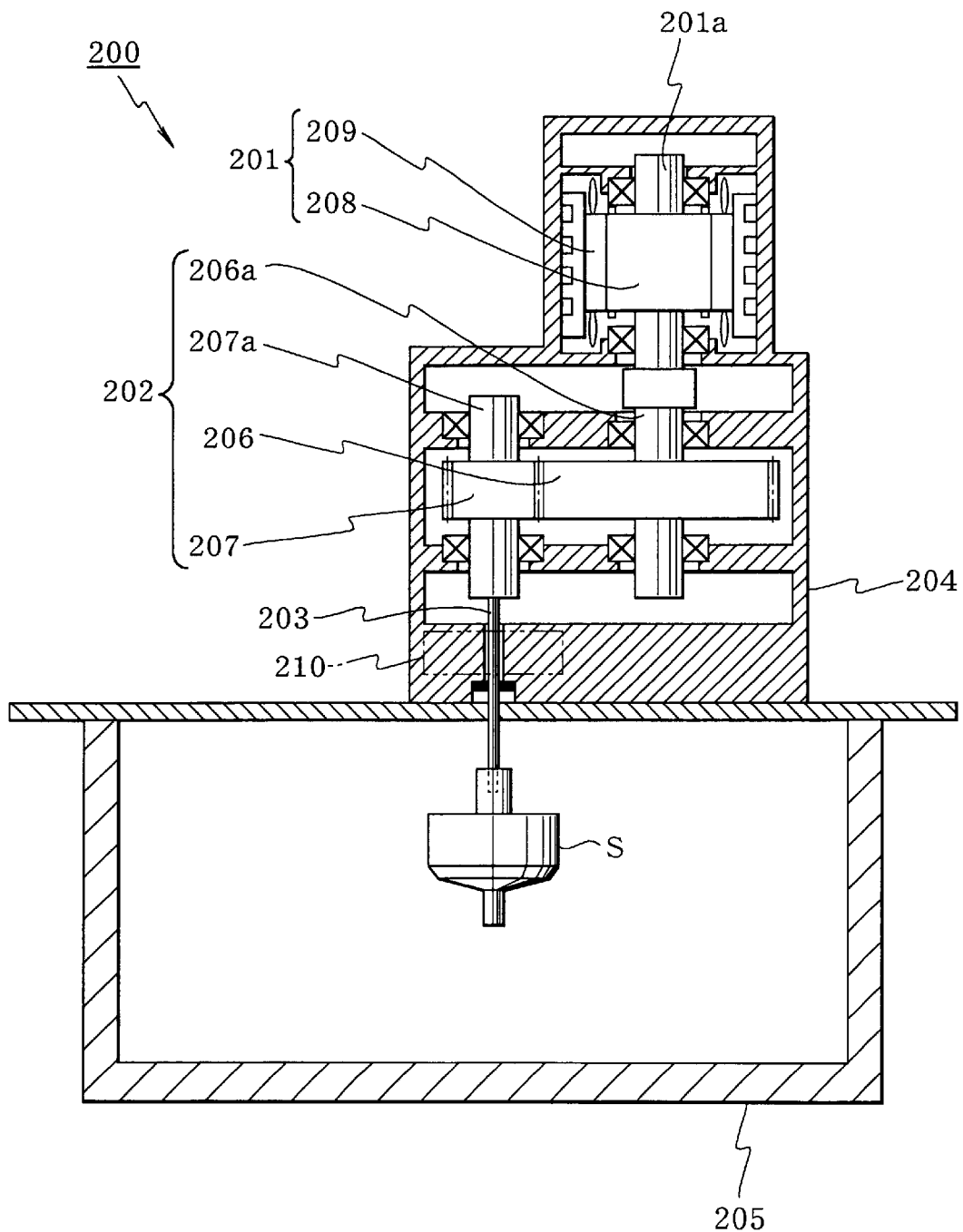
FIG. 6 is a schematic vertical sectional view of another conventional example as viewed from the front thereof.

A high-speed rotation testing apparatus 10A as a second embodiment of the present invention will be described with reference to FIG. 4. The same components of the high-speed rotation testing apparatus 10A as those of the high-speed rotation testing apparatus 10 described previously will be denoted by the same reference numerals, and duplicate descriptions will be omitted. The high-speed rotation testing apparatus 10A preferably carries out high-speed rotation tests on a test object M that is a rotating member larger and heavier than the test object S described previously.

[Second Spindle]

The high-speed rotation testing apparatus 10A comprises a second spindle 13A extended downward from the lower end of the spindle 11 (hereafter referred to as the "first spindle 11") mounted in the driving motor 20. The second spindle 13A is coupled to the first spindle 11 via a coupling 12A so that their central axes align with each other. The spindles 11 and 13A rotate integrally.

Furthermore, the high-speed rotation testing apparatus 10A has a weight supporting shaft 14A including a through-hole 15A along the center line of the apparatus. The second spindle 13A passes through the through-hole 15A in the weight supporting shaft 14A and further extends downward. The second spindle 13A engages with the damping mechanism 40 in the vicinity of its lower end, which extends into the storage container 50. The second spindle 13A has the test object M arranged at its lower end via the holding means 60 (see FIG. 2).

[Weight Supporting Shaft]

On the other hand, the weight supporting shaft 14A comprises two flange-shaped projections 14a and 14b on its outer peripheral surface and rotatably supported by a casing 30A via the thrust bearings 16A and 17A and engaging with the projections 14a and 14b.

Further, the through-hole 15A in the weight supporting shaft 14A has a square cross section in the vicinity of the upper end of the weight supporting shaft 14A and a circular cross section in the other portions thereof. Furthermore, each side of the square cross section of the through-hole is set smaller than the diameter of the circular cross section. On the other hand, like the through-hole 15A, the second spindle 13A is formed to have a square cross section in the vicinity of the upper end thereof and a circular cross section in the other portions thereof. Each side of the square cross section of the second spindle 13A is substantially as large as each side of the square cross section of the through-hole 15A so that the square cross section portion of the second spindle 13A can be inserted into the square cross section portion of the through-hole 15A. Further, the diameter of the circular cross section of the second spindle 13A is set slightly smaller than that of the circular cross section of the through-hole 15A. Furthermore, an external thread portion 13a is formed at the top of the square cross section portion. When the second spindle 13A is inserted into the weight supporting shaft 14A from below and the square cross section portion of the second spindle 13A is fitted in the square cross section portion of the trough-hole 15A, the external thread portion 13a projects from the upper end surface of the weight supporting shaft 14A. The second spindle 13A is fixed to the weight supporting shaft 14A by tightening the external thread portion 13a with a clamping nut 18A. Since the weight supporting shaft 14A and the second spindle 13A are fitted together at their square cross section portions, the second spindle 13A is rotationally driven with the weight supporting shaft 14A by the driving motor 20 via the first spindle 11.

Further, as described previously, a clearance is formed between the circular cross section portion of the through-hole 15A and the circular cross section portion of the second spindle 13A. In general, the circular cross section of the second spindle 13A has an outer diameter of 4 to 80 mm depending on the weight of the test object M. On the other hand, the clearance having a width of about 10 to 100 $\mu$m depending on the diameter of the spindle 13A. That is, this width is generally set equal to about one-eight-hundred-th to one-four-hundred-th of the outer diameter of the second spindle 13A. However, the outer diameter of the spindle 13A is not limited to this range, but may be set to have a smaller or larger value. Further, the ratio of the clearance to the outer diameter of the spindle 13A is not limited to the above-described range. Within the clearance of the through-hole 15A in the weight supporting shaft 14A, the lower end of the second spindle 13A, on which the test object M is held, can be swung using its upper end as a support point.

[Casing]

As described above, in the above described high-speed rotation testing apparatus 10A, the second spindle 13A extends downward from the first spindle 11 and engages with the weight supporting shaft 14A and the damping mechanism 40. Thus, the high-speed rotation testing apparatus comprises a casing 30A constructed differently from the casing 30. That is, the casing 30A is composed of an upper structure 31A for supporting the driving motor 20, a lower structure 32A for supporting the weight supporting shaft 14A and the damping mechanism 40, and a plurality of struts 33A that integrally couple the upper structure 31A to the lower structure 32A.

Further, the casing 30A is fixed so as to be placed on the storage container 50. When the casing 30A and the storage container 50 are installed on a horizontal surface, the casing 30 supports the rotor shaft 21, the first spindle 11, and the second spindle 13A so that they are arranged toward the vertical direction.

[Operation and Effects of the Second Embodiment]

The general operation of the high-speed rotation testing apparatus 10A constructed as described above will be described with reference to FIG. 4. First, the holding means 60 is used to install the test object M on the second spindle 13A, and the center of gravity of the test object M is then adjusted. Then, a vacuum is formed in the storage container 50 before the test object M is rotated as in the case with the high-speed rotation testing apparatus 10, described previously.

When the center of gravity of the test object M is offset from the center line of the rotor shaft 21, the second spindle 13A may be bent during high speed rotation. However, the second spindle 13A is gently bent between the lower end of the second spindle 13A and the junction between the second spindle 13A and the weight supporting shaft 14A. This effectively avoids the concentration of stress at one location of the second spindle 13A, which may cause the spindle to be broken down. Further, since the swing caused by the bending of the second spindle 13A is damped by the damping mechanism 40, located in the vicinity of the lower end of the spindle, the test object M can be stably rotated at high speed even if its center of gravity is slightly offset from the center line of the rotor shaft 21. Furthermore, the second spindle 13A is supported by the casing 30A via the weight supporting shaft 14A and the thrust bearings 16A and 17A, so that even if the second spindle 13A swings, the effects of this swing on the rotor shaft 21 of the driving motor 20 can be eliminated.

As described above, the high-speed rotation testing apparatus 10A has effects similar to those of the high-speed rotation testing apparatus 10. Further, the weight supporting shaft 14A coupled to the second spindle 13A is supported on the casing 30A via the thrust bearings 16A and 17A. Consequently, even if a heavy test object M is installed on the second spindle 13A, this load is imparted to the casing 30A. Therefore, the effects of the load on the rotor shaft 21 of the driving motor 20 can be eliminated, thereby enabling the heavy test object M to be subjected to high-speed rotation stets.

According to the aspect of the present invention, a through-hole is formed in a rotor shaft of a driving motor so as to form a clearance in which a spindle can swing. The spindle is inserted into the through-hole, the upper ends of the spindle and the rotor shaft are coupled together, and the spindle has a damping mechanism arranged in the vicinity of its lower end. Accordingly, even if the center of gravity of a test object held by the spindle is offset from the center line of the rotor shaft, the spindle swings by being gently bent between its upper and lower ends, thereby preventing the concentration of stress on the spindle, which may cause the spindle to be broken down. Further, the spindle swings around the junction between the spindle and the rotor shaft, and this swing is damped by the damping mechanism. Consequently, the effects of the swing on the rotor shaft can be minimized.

Accordingly, while producing these effects, torque can be applied directly to the spindle by the driving motor, thereby eliminating the need for the interposition of a gear train. Thus, the present invention can eliminate mechanical friction losses associated with a gear train, thereby allowing the test object to be efficiently rotated at high speed and reducing power consumption. Further, the number of mechanical parts required is reduced, thereby improving productivity and facilitating maintenance. Furthermore, noise or vibration associated with a gear train can be prevented. Moreover, the rotation speed of the test object can be promptly increased to the target value to reduce the time required for the tests. Therefore, the present invention is preferable for high-speed rotation tests requiring a long-time cyclic operation.

Further, since the present invention uses no air turbine as in the prior art, high power consumption by a compressor never occurs, or no action need be taken for possible heat from a compressor. Furthermore, it should be appreciated that the driving motor enables the rotation speed to be easily controlled.

Moreover, according to the second aspect of the present invention, a through-hole is formed in a weight supporting shaft arranged under a spindle so as to form a clearance in which the spindle can swing. The spindle is inserted into the through-hole, the upper ends of the spindle and the weight supporting shaft are coupled together, and the spindle has a damping mechanism arranged in the vicinity of its lower end. Accordingly, even if the center of gravity of a test object held by the spindle is offset from the center line of the rotor shaft, the spindle swings by being gently bent between its lower end and the junction between the spindle and the weight supporting shaft, thereby preventing the concentration of stress on the spindle, which may cause the spindle to be broken down. Furthermore, the spindle swings around the junction between the spindle and the weight supporting shaft, and this swing is damped by the damping mechanism. Moreover, the weight supporting shaft is supported by the frame via bearings, thereby preventing the swing from being transmitted upward from the junction. Thus, the effects of the swing on the rotor shaft can be eliminated. Therefore, the aspect of the present invention has effects similar to those of the aspect of the above described invention.

Furthermore, according to the second aspect of the present invention, the weight supporting shaft coupled to the spindle is supported by a frame via thrust bearings, the load of the spindle is imparted to the frame. Accordingly, in addition to the above effects, the aspect of the invention can eliminate the effects of the load on the rotor shaft of the driving motor, enabling even a heavy test object to be subjected to high-speed rotation tests.

Further, if the damping mechanism of the aspect of the invention is constituted by a storage chamber filled with a lubricant, a housing arranged inside the storage chamber, and journal chambers, then viscous resistance offered by the lubricant while the housing is swing can be imparted to the spindle, thereby effectively restraining the spindle from swing.

Further, if the constriction of the present invention includes a storage chamber for preventing crushed pieces, then it serves to prevent the scattering of crushed pieces of the test object broken down during high speed rotation. If the storage container is a vacuum vessel, high-speed rotation tests can be carried out without any windage loss. Consequently, the tests can be concentrated on the effects on the test object during high-speed rotational movement, and the rotation speed can be promptly increased.

The present invention is constituted and functions as described above, thereby providing an unprecedented excellent high-speed rotation testing apparatus.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2001-41694 (Filed on Feb. 19, 2001) including specification, claims, drawings and summary are incorporated herein by reference in its entirety.

What is claimed is:

1. A high-speed rotation testing apparatus for rotating a test object to test at least one of strength and durability of the test object while rotating, the apparatus comprising:

a spindle comprising a lower end that holds the test object;

a driving motor that applies torque to the spindle, the driving motor comprising a rotor shaft that defines a through-hole configured to receive said spindle, a clearance between an inner diameter of said through-hole and an outer diameter of a lower portion of said spindle enables an oscillation of said spindle within said through-hole during rotation;

a frame that supports the rotor shaft of the driving motor in a substantially vertical orientation; and a damping mechanism, configured to suppress the oscillation of said spindle within said through-hole;

wherein an upper end of said spindle is coupled to an upper end of said rotor shaft, so that said driving motor directly drives said spindle.

2. The high-speed rotation testing apparatus according to claim 1, wherein said damping mechanism comprises:

a journal bearing configured to cooperate with said spindle;

a housing that supports said journal bearing; and a storage chamber, containing a lubricant and said housing so that said housing oscillates with said spindle.

3. The high-speed rotation testing apparatus according to claim 1, further comprising a storage container that houses the test object and contains pieces of the test object when the test object fails.

4. The high-speed rotation testing apparatus according to claim 2, further comprising a storage container that houses the test object during testing and contains pieces of the test object when the test object fails.

5. The high-speed rotation testing apparatus according to claim 3, wherein said storage container comprises a vacuum configured to discharge internal gas.

6. The high-speed rotation testing apparatus according to claim 4, wherein said storage container comprises a vacuum configured to discharge internal gas.

7. The high-speed rotation testing apparatus according to claim 1, wherein the upper end of said spindle comprises a substantially square cross-section configured to fit within a corresponding substantially square cross-section of an upper end of the through-hole, connecting the upper end of said spindle and the upper end of said rotor shaft.

8. A high-speed rotation testing apparatus for rotating a test object to test at least one of strength and durability of the test object while rotating, the apparatus comprising:

a first spindle;

a second spindle coupled to a lower end of said first spindle and comprising a lower end that holds the test object, center lines of the first spindle and the second spindle being aligned;

a driving motor that applies torque to said first spindle, the driving motor comprising a rotor shaft coupled to an upper end of said first spindle, the rotor shaft defining a through-hole configured to receive a portion of said first spindle, said first spindle rotating integrally with said rotor shaft in said through-hole;

a weight supporting shaft, defining a through-hole configured to receive a portion of said second spindle, said second spindle rotating integrally with said first spindle within said through-hole;

a frame that supports said rotor shaft and said weight supporting shaft in a substantially vertical configuration; and a damping mechanism, configured to suppress an oscillation of said second spindle within said through-hole during rotation.

9. The high-speed rotation testing apparatus according to claim 8, wherein said damping mechanism comprises:

a journal bearing configured to cooperate with said second spindle;

a housing that supports said journal bearing; and a storage chamber, containing a lubricant and said housing so that said housing oscillates with said second spindle.

10. The high-speed rotation testing apparatus according to claim 8, further comprising a storage container that houses the test object during testing and contains pieces of the test object when the test object fails.

11. The high-speed rotation testing apparatus according to claim 9, further comprising a storage container that houses the test object during testing and contains pieces of the test object when the test object fails.

12. The high-speed rotation testing apparatus according to claim 10, wherein said storage container comprises a vacuum configured to discharge internal gas.

13. The high-speed rotation testing apparatus according to claim 11, wherein said storage container comprises a vacuum configured to discharge internal gas.

14. The high-speed rotation testing apparatus according to claim 8, wherein the upper end of said second spindle comprises a substantially square cross-section configured to fit within a corresponding substantially square cross-section of an upper end of said through-hole, enabling the upper end of the spindle to be joined with the upper end of the rotor shaft.

15. The high-speed rotation testing apparatus according to claim 8, wherein a clearance between an outer diameter of said second spindle and an inner diameter of said through-hole enables an oscillation of said second spindle within said through-hole during rotation of the test object, relieving a stress on said second spindle.

16. A rotation testing apparatus for rotating a test object to test at least one of strength and durability of the test object while rotating, the apparatus comprising:

a driving motor, comprising a rotor shaft that defines a center through-hole; and a spindle, joined at an upper end with an upper end of the rotor shaft and joined at a lower end with the test object, the spindle extending through the through-hole of the rotor shaft, the driving motor applying torque to the spindle to rotate the test object.

17. The rotation testing apparatus according to claim 16, wherein the upper end of the spindle comprises a substantially square cross-section configured to fit within a corresponding substantially square cross-section of an upper end of the through-hole, connecting the upper end of the spindle and the upper end of said rotor shaft.

18. The rotation testing apparatus according to claim 16, wherein a clearance between an outer diameter of the spindle and an inner diameter of the through-hole enables an oscillation of the spindle within the through-hole during rotation of the test object, relieving a stress on the spindle.

19. The rotation testing apparatus according to claim 18, further comprising a damper configured to suppress the oscillation of the spindle within the through-hole.

20. The rotation testing apparatus according to claim 19, the damper comprising a chamber containing a lubricant, wherein the oscillation of the spindle is suppressed in accordance with a flow resistance of the lubricant.

21. The rotation testing apparatus according to claim 20, the chamber further containing a journal bearing corresponding to said spindle and a housing supporting the journal bearing, wherein the housing oscillates with the spindle when the spindle is rotating, and wherein the oscillation of the spindle is suppressed in accordance with the flow resistance of the lubricant between the spindle and the journal bearing and between the journal bearing and the housing.

* * * * *